US009078890B2

(12) United States Patent
Yu et al.

(10) Patent No.: US 9,078,890 B2
(45) Date of Patent: Jul. 14, 2015

(54) USE OF KOUMINE AND ITS HOMOLOGUES IN PREPARATION OF MEDICAMENT FOR TREATMENT OF AUTOIMMUNE DISEASES OF INVOLVED BONES AND JOINTS

(71) Applicant: Fujian Medical University, Fuzhou (CN)

(72) Inventors: Changxi Yu, Fuzhou (CN); Ying Xu, Fuzhou (CN); Jian Yang, Fuzhou (CN); Yanping Su, Fuzhou (CN); Hongda Cai, Fuzhou (CN)

(73) Assignee: Fujian Medical University, Fuzhou (CN)

( * ) Notice: Subject to any disclaimer, the term of this patent is extended or adjusted under 35 U.S.C. 154(b) by 0 days.

(21) Appl. No.: 14/138,978

(22) Filed: Jul. 16, 2014

(65) Prior Publication Data

US 2015/0011767 A1 Jan. 8, 2015

Related U.S. Application Data

(63) Continuation-in-part of application No. PCT/CN2011/080347, filed on Sep. 29, 2011.

(30) Foreign Application Priority Data

Jun. 25, 2011 (CN) .......................... 2011 1 0174657

(51) Int. Cl.
    *A61K 31/439* (2006.01)
    *A61K 31/4748* (2006.01)
(52) U.S. Cl.
    CPC ........... *A61K 31/4748* (2013.01); *A61K 31/439* (2013.01)
(58) Field of Classification Search
    USPC ................................................. 514/279, 825
    See application file for complete search history.

(56) References Cited

FOREIGN PATENT DOCUMENTS

| CN | 101322705 A | 12/2008 |
|---|---|---|
| CN | 101323618 B | 12/2008 |
| CN | 102240287 A | 11/2011 |

OTHER PUBLICATIONS

Rasool, M. et al., Anti-inflammatory effect of *Spirulina fusiformis* on adjuvant-induced arthritis in mice, *Biol Pharm Bull*, 29(12): 2483-2487, 2006.

Sun, L. et al., Inhibitory effects of koumine on splenocyte proliferation and humoral immune response in mice, *Pharmacology and Clinics of Chinese Materia Medica*, 15(6): 10-12, 1999.
Wu, D. et al., Antitumor activity of koumine in vitro and vivo, *Pharmacology and Clinics of Chinese Materia Medica*, 22 (5): 6-8, 2006.
Xu, S. et al., Methodology of Pharmacological Experiment, People's Medical Publishing House, 3 Ed: 912-913, 2002.
Yang, H. et al. Measuring Device for Rat Paw Swelling Volume and Detection Accuracy Control, *Journal of Chengde Medical University*, 19 (2):132-133, 2002.
English abstract translation of CN-101322705A, Applications of Koumine in Preparing Medicament for Treating Chronic Ache, published Dec. 17, 2008.
English abstract translation of CN-101323618B, Method for Separating and Preparation of Gelsemium Elegans Alkaloid Monomer by High Speed Counter Current Chromatography, published Dec. 17, 2008.
English abstract translation of CN-102240287A, Applications of Gelsemine, Koumine and 1-Methoxyl Gelsemine to Preparation of Medicine for Treating Anxiety, published Nov. 16, 2011.
Brief explanation of Yang, H. et al. Measuring Device for Rat Paw Swelling Volume and Detection Accuracy Control, *Journal of Chengde Medical University*, 19 (2):132-133, 2002.
Brief explanation of Xu, S. et al., Methodology of Pharmacological Experiment, People's Medical Publishing House, 3 Ed: 912-913, 2002.

*Primary Examiner* — Charanjit Aulakh
(74) *Attorney, Agent, or Firm* — Gifford, Krass, Sprinkle, Anderson & Citkowski, P.C.

(57) ABSTRACT

The present invention discloses an application of koumine and homologue thereof in preparation of drugs for treating autoimmune diseases involving bones and joints including rheumatoid arthritis, spondylitis ankylopoietica or the like, in particular an application of *Gelsemium* alkaloid monomer koumine and homologue thereof or pharmaceutically acceptable salt thereof as active ingredient in preparation of drugs for treating autoimmune diseases involving bones and joints including rheumatoid arthritis, spondylitis ankylopoietica or the like. The result of pharmacology experiment shows that koumine can decrease the generation of organism antibody against autoimmune diseases involving bones and joints in a dose dependent manner, improve symptoms of swelling and hyperalgesia, reduce arthritis index, reverse joint pathological changes, and has no serious shortage of commonly used clinical drugs; thus koumine has an effect against autoimmune diseases involving bones and joints including rheumatoid arthritis, ankylosing spondylitis etc. with strong potency and low toxicity. Koumine can be developed into a new drug for treating autoimmune disease involving bones and joints including rheumatoid arthritis, spondylitis ankylopoietica etc., which has a clear industrial prospect.

1 Claim, 7 Drawing Sheets

Drawings of the Description

USE OF KOUMINE AND ITS HOMOLOGUES IN PREPARATION OF MEDICAMENT FOR TREATMENT OF AUTOIMMUNE DISEASES OF INVOLVED BONES AND JOINTS

FIELD OF THE INVENTION

The invention relates to a new use of *Gelsemium* alkaloid monomer koumine and homologues thereof, in particular to an application of koumine and homologues thereof in preparation of drugs for treating autoimmune diseases involving bones and joints including rheumatoid arthritis, ankylosing spondylitis etc.

BACKGROUND OF THE INVENTION

Rheumatoid arthritis is a multisystemic inflammatory autoimmune diseases mainly involving bones and joints, and the disease also includes ankylosing spondylitis; the pathogenesis of the disease is unknown. Clinically, the most common inflammatory joint disease is rheumatoid arthritis, and ankylosing spondylitis is in the next place. They seriously affect patient's functional status, quality of life and life expectancy. Because of their chronicity feature, related complication and long-term dysfunction, they have huge influence on society and economy. Now, the main treatment for autoimmune diseases involving bones and joints including rheumatoid arthritis, ankylosing spondylitis etc. is medication (commonly used drugs are non-steroidal anti-inflammatory drugs, and newly-marketed biopreparate such as TNF-α inhibitor), but none of these drugs can completely control the development of patient's condition, and they have serious side effects. Therefore, there is an urgent need for developing new type of drug to treat autoimmune diseases involving bones and joints including rheumatoid arthritis, ankylosing spondylitis etc. One of R&D hot spots and directions is to search for active medicinal substance in Chinese herbs.

*Gelsemium elegans* Benth., a medicinal plant of a long history, is the whole plant of Loganiaceae plant *Gelsemium elegans* Benth, which abounds in Fujian, Zhejiang, Guangdong etc. of China. *Gelsemium* has various physiological and pharmacological activities, such as functions of anti-tumor, relaxing smooth muscle, suppressing platelet aggregation etc.; but it has stronger toxicity and is not suitable for direct use in medicine. The main active ingredient of *Gelsemium* is alkaloid, including more than 40 kinds of homologue monomers such as koumine, gelsemine and gelsenicine etc. Although the total alkaloidal toxicity of *Gelsemium* is high, the toxicity of each monomers is different. The koumine is an effective ingredient which has the highest content and less toxicity in domestic *Gelsemium* alkaloid monomers, which has a good prospect of development and application.

Koumine, with the molecular formula as $C_{20}H_{22}N_2O$, has the following structural formula:

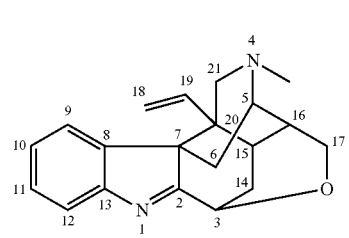

The main source of koumine is *Gelsemium*, from which the koumine can be extracted and separated, for example, by use of column chromatography, or of the method recited in the patent "The Method of Separating and Preparing *Gelsemium* Alkaloid Monomer from *Gelsemium* by High Speed Counter-Current Chromatography" invented by this inventor (granted, Patent No. CN101323618B), which provides a way to obtain koumine efficiently and quickly, and lays the foundation of industry application of koumine.

In more recent years, the researches on koumine are increasing. It is found that koumine has various physiological and pharmacological activities such as anti-tumor effect [Darong Wu, Rui Qin, Jing Cai, Debiao Chi. *The research on anti-tumor effect of koumine*, Pharmacology and Clinics of Chinese Materia Medica, 2006, 22 (5): 6-8], anti-anxiety effect (a China patent application has been filed: the application of gelsemine, koumine, gelsevirine in preparation of drugs for treating anxiety, patent No. ZL 201110130826.6), anti-chronic pain effect (a China patent application has been filed: the application of koumine as only active ingredient in preparation of drugs for treating chronic pains, patent No. ZL 200810071467.X) etc. However, the effect of koumine against autoimmune diseases including rheumatoid arthritis or the like and possible use thereof have not been reported in literatures and patents. This patent application discloses an effect of koumine against rheumatoid arthritis and an application of the koumine in preparation of drugs for treating autoimmune diseases involving bones and joints including rheumatoid arthritis, ankylosing spondylitis etc.

SUMMARY OF THE INVENTION

In order to overcome the shortage of prior art, the object of the invention is to provide a new method of use of *Gelsemium* alkaloid monomer koumine against autoimmune diseases involving bones and joints including rheumatoid arthritis, ankylosing spondylitis etc. with strong efficiency and low toxicity, i.e. the application of koumine and homologues thereof or pharmaceutically acceptable salt thereof as active ingredient in preparation of drugs for treating autoimmune diseases involving bones and joints including rheumatoid arthritis, ankylosing spondylitis etc.

The technical solution of the application for solving the technical problems is to use koumine as active ingredients in preparation of drugs for treating autoimmune diseases involving bones and joints including rheumatoid arthritis, ankylosing spondylitis etc.

The koumine is *Gelsemium* alkaloid monomer, and the molecular formula is $C_{20}H_{22}N_2O$, having structural formula of:

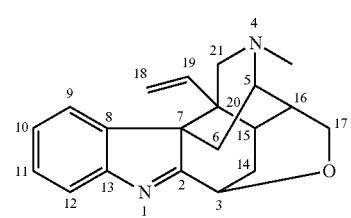

Koumine or pharmaceutically acceptable salt thereof have a use in preparation of drugs for treating autoimmune diseases involving bones and joints including rheumatoid arthritis, ankylosing spondylitis etc.

The result of pharmacology experiment shows that koumine can decrease the production of organism antibody leading to rheumatoid arthritis in a dosage-dependent manner, improve symptoms of swelling and hyperalgesia, reduce an arthritis index, and reverse joint pathological changes, which indicates that koumine has strong efficiency and low toxicity against autoimmune diseases involving bones and joints including rheumatoid arthritis, ankylosing spondylitis etc.

The preferred technical solution of the invention is to use *Gelsemium* alkaloid monomer koumine having following structural formula or pharmaceutically acceptable salt thereof as active ingredients in preparation of drugs for treating autoimmune diseases involving bones and joints including rheumatoid arthritis, ankylosing spondylitis etc.

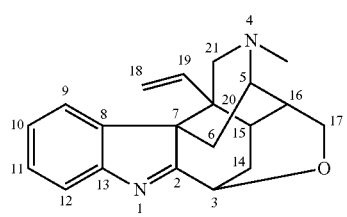

The benefit of the invention:

1. Koumine has a potent effect against autoimmune diseases involving bones and joints including rheumatoid arthritis, ankylosing spondylitis etc., which not only remarkably relieves symptoms, such as swelling, hyperalgesia condition, and arthritis index, but also reverses joint pathological damage and reduces organism antibody level. That is "treating both symptoms and root causes". The invention overcomes the defect of non-steroidal anti-inflammatory drugs in prior art which "treat the symptoms but not the root causes".

2. Koumine has low toxicity (mice, subcutaneous injection, $LD_{50}$=99.0 mg/kg), far below total *Gelsemium* alkaloidal toxicity (mice, subcutaneous injection, $LD_{50}$=1.68 mg/kg), and overcomes the shortage of clinical commonly used drugs in prior art, such as overcomes the serious gastrointestinal tract adverse reaction caused by non-steroidal anti-inflammatory drugs, and the risks of easy degradation, causing tuberculosis, tumour or the like of biopreparate.

3. There is a potential significant economic effect. Now, there is a huge market of therapeutic drugs for autoimmune diseases involving bones and joints including rheumatoid arthritis, ankylosing spondylitis etc. world-wide. Some data show that the expense of a rheumatoid arthritis patient is about 61000-122000 dollars more than a normal person in a life time. Koumine and homologues thereof or pharmaceutically acceptable salt thereof have an application in preparation of drugs for treating autoimmune diseases involving bones and joints including rheumatoid arthritis or the like, and if developed in accordance to National Innovative Drug Ratification Measures, it is expected to be a registration category 1 new drug of Chinese independent intellectual property for treating autoimmune diseases involving bones and joints including rheumatoid arthritis, ankylosing spondyliti or the like with strong potency and low toxicity, which has a clear industrial prospect.

4. The koumine of the invention comes from natural plant *Gelsemium* by extraction and purification, and China is abound in *Gelsemium* plant, thus can promote the development of related medical materials industry.

BRIEF DESCRIPTION OF THE DRAWINGS

FIG. 3-1 is the result graph of false modeling group in the reverse effect experiment of koumine on adjuvant arthritis mice joint pathological damage. FIG. 3-2 is the result graph of negative control group in the reverse effect experiment of koumine on adjuvant arthritis mice joint pathological damage. FIG. 3-3 is the result graph of indomethacin positive control group in the reverse effect experiment of koumine on adjuvant arthritis mice joint pathological damage. FIG. 3-4 is the result graph of 0.8 mg/kg koumine group in the reverse effect experiment of koumine on adjuvant arthritis mice joint pathological damage. FIG. 3-5 is the result graph of 4 mg/kg koumine group in the reverse effect experiment of koumine on adjuvant arthritis mice joint pathological damage. FIG. 3-6 is the result graph of 20 mg/kg koumine group in the reverse effect experiment of koumine on adjuvant arthritis mice joint pathological damage.

FIG. 4 is a schematic diagram of a homemade paw volumenometer.

FIG. 5 is a graph of the inhibiting effect of koumine on serum type II collagen antibody of type II collagen-induced arthritis rat. In the figure, the horizontal ordinate represents groups, the vertical ordinate represents the level of serum type II collagen antibody (ng/ml); 1 is negative control group, 2 is amethopterin positive control group, 3 is 0.6 mg/kg koumine group, 4 is 3 mg/kg koumine group, 5 is 15 mg/kg koumine group, 6 is false modeling group; compared with false modeling group, $^{\#\#\#}P<0.01$; compared with negative control group, $*P<0.05$, $**P<0.01$.

FIG. 6 is a graph of the inhibiting effect of koumine on paw swelling of type II collagen-induced arthritis rat. In the figure, the horizontal ordinate represents interventional time (day), the vertical ordinate represents paw volume (ml); 1 is negative control group, 2 is amethopterin positive control group, 3 is 0.6 mg/kg koumine group, 4 is 3 mg/kg koumine group, 5 is 15 mg/kg koumine group, 6 is false modeling group; compared with false modeling group, $^{\#\#\#}P<0.01$; compared with negative control group, $**P<0.01$; compared with the situation before intervention, $\star P<0.05$, $\star\star P<0.01$.

FIG. 8-1-1 is a lateral position X-ray film of an effect of koumine against type II collagen-induced arthritis rat joint pathological damage of false modeling group. FIG. 8-1-2 is a anteroposterior X-ray film of an effect of koumine against type II collagen-induced arthritis rat joint pathological damage of false modeling group. FIG. 8-2-1 is a lateral position X-ray film of an effect of koumine against type II collagen-induced arthritis rat joint pathological damage of negative control group. FIG. 8-2-2 is a anteroposterior X-ray film of an effect of koumine against type II collagen-induced arthritis rat joint pathological damage of negative control group. FIG. 8-3-1 is a lateral position X-ray film of an effect of koumine against type II collagen-induced arthritis rat joint pathological damage of positive control group. FIG. 8-3-2 is a anteroposterior X-ray film of an effect of koumine against type II collagen-induced arthritis rat joint pathological damage of positive control group. FIG. 8-4-1 is a lateral position X-ray film of an effect of koumine against type II collagen-induced arthritis rat joint pathological damage of 0.6 mg/kg koumine group. FIG. 8-4-2 is a anteroposterior X-ray film of an effect of koumine against type II collagen-induced arthritis rat joint pathological damage of 0.6 mg/kg koumine group. FIG. 8-5-1 is a lateral position X-ray film of an effect of koumine against type II collagen-induced arthritis rat joint pathological damage of 3 mg/kg koumine group. FIG. 8-5-2 is a anteroposterior X-ray film of an effect of koumine against type II collagen-induced arthritis rat joint pathological damage of 3 mg/kg koumine group. FIG. 8-6-1 is a lateral position X-ray film of an effect of koumine against type II collagen-induced arthritis rat joint pathological damage of 15 mg/kg koumine group. FIG. 8-6-2 is a anteroposterior X-ray film of an effect of koumine against type II collagen-induced arthritis rat joint pathological damage of 15 mg/kg koumine group.

FIG. 9-1 is a false modeling group HE staining histochemistry result graph of an effect of koumine against type II collagen-induced arthritis rat joint pathological damage. FIG. 9-2 is a negative control group HE staining histochemistry result graph of an effect of koumine against type II collagen-induced arthritis rat joint pathological damage. FIG. 9-3 is a positive control group HE staining histochemistry result graph of an effect of koumine against type II collagen-induced arthritis rat joint pathological damage. FIG. 9-4 is a 0.6 mg/kg koumine group HE staining histochemistry result graph of an effect of koumine against type II collagen-induced arthritis rat joint pathological damage. FIG. 9-5 is a 3 mg/kg koumine group HE staining histochemistry result graph of an effect of koumine against type II collagen-induced arthritis rat joint pathological damage. FIG. 9-6 is a 15 mg/kg koumine group HE staining histochemistry result graph of an effect of koumine against type II collagen-induced arthritis rat joint pathological damage.

DETAILED DESCRIPTION OF THE EMBODIMENTS

Figure 1:
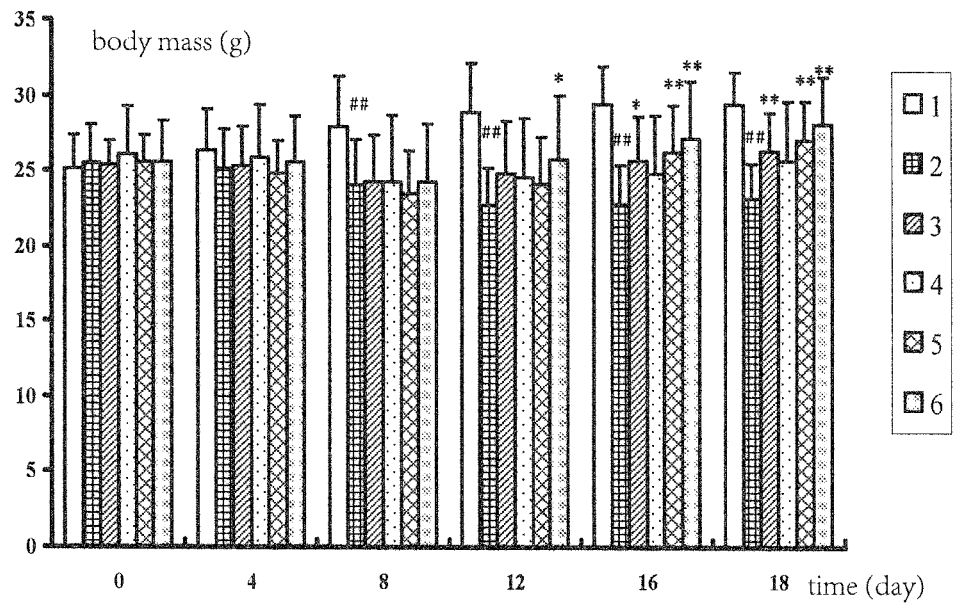
FIG. 1 is a graph of the improving effect of koumine on the body weight of adjuvant arthritis mice. In the figure, the horizontal ordinate represents time (day), the vertical ordinate represents body mass (gram); 1 is false modeling group, 2 is physiological saline negative control group, 3 is indomethacin positive control group, 4 is 0.8 mg/kg koumine group, 5 is 4 mg/kg koumine group, 6 is 20 mg/kg koumine group; compared with false modeling group, $^{\#\#\#}P<0.01$; compared with negative control group, $*P<0.05$, $**P<0.01$.

Hereinafter, the invention is further described in conjunction with Examples.

Example 1

The Therapeutic Effect of Koumine on Adjuvant Arthritis in Mice

Adjuvant arthritis induced by complete Freund's adjuvant is similar to human autoimmune diseases involving bones and joints, therefore, it is considered as an ideal model for the study of human autoimmune diseases involving bones and joints. Example 1 is based on adjuvant arthritis model in mice, and uses arthritis symptoms (the condition, body weight, phlogogenic paw swelling degree, hyperalgesia of mice) and joint pathological changes as indicators to illustrate the therapeutic effect of koumine on autoimmune diseases involving bones and joints including rheumatoid arthritis, ankylosing spondylitis etc.

1 Materials
1.1 Animals

Kunming mice, 18-23 g, purchased from Shanghai Slac Laboratory Animal Co. Ltd., License No.: SCXK (Shanghai) 2009-0005. The mice are maintained on a 12/12 h light-dark cycle at constant temperature ($23\pm2°$ C.) and constant humidity ($50\pm5\%$) with food and water ad libitum. 3 days after adapted to the laboratory, they are used in formal experiment, the experiment operation of which follows the rules issued by international and local experimental animal use and protection committee (similarly hereinafter).

1.2 Drugs and Reagents

Koumine is obtained from natural plant *Gelsemium* by extraction and separation by the applicant of the invention, the purity is >99% (accurately weighted koumine is dissolved in 0.2 mol/L HCl, adjusted to pH=7 with 5 mol/L sodium hydroxide, and diluted with physiological saline to desired solutions of each dosage group). Indomethacin, purchased from Shanghai Jiufu Pharmaceutical Co. Ltd. Complete Freund's adjuvant, purchased from Sigma Company. BCG freeze-dried powder, purchased from Shanghai Biological Product Company.

1.3 Laboratory Instruments

Micro syringe, purchased from U.S. Hamilton. Type PL-200 thermal dolorimeter, purchased from Chengdu Taimeng Science And Technology Co., Ltd. Precision electronic balance, purchased from AND Company, Japan. Precision acidity meter, purchased from Shanghai Dapu Instruments Co., Ltd. Vernier calipers, purchased from Shanghai Sanfeng Machinery Company. Full automatic cryo-cut cryostat microtome, purchased from Leica, Germany. BX51 microscope, purchased from OLYMPUS, Japan. (Similarly hereinafter).

2 Procedures

BCG was inactivated in water bath at 80° C., and fully emulsified along with complete Freund's adjuvant to form complete Freund's adjuvant emulsion containing 5 mg/ml BCG, preserved at 4° C., and shake well before use. The Kunming mice were divided into a modeling group and a false modeling group. According to the method recited in the literature [Rasool M, Sabina E P, Lavanya B. *Anti-inflammatory effect of Spirulina fusiformis on adjuvant-induced arthritis in mice*. Biol Pharm Bull. 2006, 29(12):2483-7], for the modeling group, the model was prepared by intradermal injection of 20 ul the emulsion under the plantar surface of right paws after the mice was narcotized; for the false modeling group, the emulsion was replaced with physiological saline. For the modeling group, the animals were screened on Day 8 after injection: the mice with the injected paw thickness increased >0.5 mm and thermal hyperalgesia occurred (paw thermal withdrawal latency <8 second) were selected as experimental subjects. The selected mice were divided into 5 groups randomly: low, middle, high dose treatment group (0.8, 4, 20 mg/kg); indomethacin positive control group (10 mg/kg); negative control group (physiological saline), each comprising 12 animals. Day 8 after inflammation, intragastric administration was carried out on each group to give corresponding intervention, one time per day for 10 days continuously.

Observation Indicators:

(1) Observation on the Influence of Koumine on Symptoms of Adjuvant Arthritis Mice ① Observation on the Influence of Koumine on the Condition and Body Weight of Adjuvant Arthritis Mice The condition of the mice in each group were observed after inflammation, and the changes of body weight of the mice were observed by weighing before inflammation and on Day 4, Day 8, Day 12, Day 16, Day 18 after inflammation.

② Observation on the Influence of Koumine on the Degree of Phlogogenic Paw Swelling of Adjuvant Arthritis Mice According to Methodology of Pharmacological Experiment (Shuyun Xu, Rulian Bian: *Methodology of Pharmacological Experiment* [M], 3rd Ed., People's Medical Publishing House: 912-913), paw thickness was selected as a paw swelling index and was measured using vernier caliper, measuring timing is the same as above, each measurement repeats 3 times and the average was taken (similarly hereinafter).

3. Results 3.1 The Effect of Koumine on Symptoms of Adjuvant Arthritis Mice

① the Influence of Koumine on the Condition and Body Weight of Adjuvant Arthritis Mice After inflammation, the food intake and activity of negative control group decreased obviously, while no obvious change was observed in koumine treatment group; the body weight of mice in each group on Day 4, Day 8, Day 12, Day 16, Day 18 after inflammation were shown as in FIG. 1. The results show that koumine has a dose dependent antagonistic effect on body weight reducing of adjuvant arthritis mice, even robustness-promoting effect on high-dose group.

Figure 2:
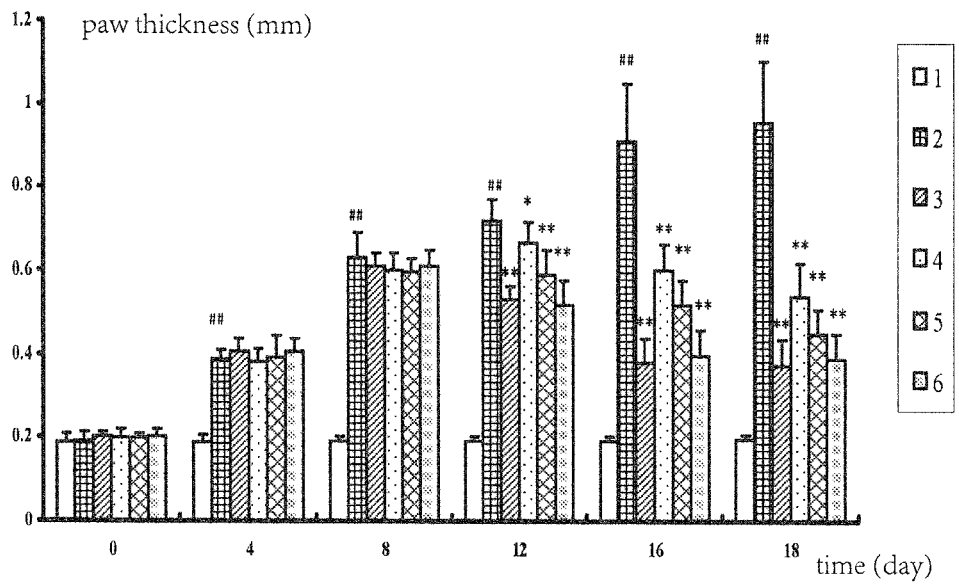
FIG. 2 is a graph of inhibiting effect of koumine on phlogogenic paw swelling of adjuvant arthritis mice. In the figure, the horizontal ordinate represents time (day), the vertical ordinate represents paw thickness (mm); 1 is false modeling group, 2 is physiological saline negative control group, 3 is indomethacin positive control group, 4 is 0.8 mg/kg koumine group, 5 is 4 mg/kg koumine group, 6 is 20 mg/kg koumine group; compared with false modeling group, $^{\#\#\#}P<0.01$; compared with negative control group, $*P<0.05$, $**P<0.01$.

② The Influence of Koumine on the Degree of Phlogogenic Paw Swelling of Adjuvant Arthritis Mice The degree of mice phlogogenic paw swelling of each group on Day 4, Day 8, Day 12, Day 16, Day 18 after inflammation were shown as in FIG. 2. The results show that koumine reduces the phlogogenic paw thickness of adjuvant arthritis mice in dose and time-dependent manner, indicating that koumine has an effect of improving the swelling symptoms of adjuvant arthritis.

③ The Influence of Koumine on Hyperalgesia of Adjuvant Arthritis Mice

Phlogogenic paw thermal stimulus withdrawal latency were shown in Table 1, the results show that koumine can significantly extend the thermal stimulus withdrawal latency of adjuvant arthritis mice, and there was a dose-effect and time-effect relationships, indicating koumine has an effect against the hyperalgesia of adjuvant arthritis.

TABLE 1 the antagonistic effect of koumine on hyperalgesia of adjuvant arthritis mice ($\bar{x} \pm s$, n = 12)

| Group | Before intervention | Thermal stimulus withdrawal latency (second) Intervention | | | | |
|---|---|---|---|---|---|---|
| | | Day 4 | Day 8 | Day 12 | Day 16 | Day 18 |
| False modeling | 14.3 ± 1.5 | 14.4 ± 1.0 | 14.1 ± 1.0 | 13.3 ± 0.9 | 13.8 ± 1.1 | 14.0 ± 1.0 |
| Negative control | 14.2 ± 1.2 | 5.9 ± 0.8##★★ | 4.3 ± 1.3##★★ | 4.2 ± 0.9##★ | 3.5 ± 1.5##★ | 3.6 ± 1.0##★★ |
| Positive control | 13.8 ± 1.2 | 5.9 ± 1.1★★ | 4.1 ± 0.8★★ | 8.9 ± 0.9**★ | 9.8 ± 1.6**★ | 10.1 ± 1.2**★★ |
| Koumine treatment | | | | | | |
| 0.8 mg/kg | 14.1 ± 1.1 | 5.9 ± 1.3★★ | 4.9 ± 1.1★★ | 4.9 ± 1.0*★ | 5.9 ± 1.0**★ | 6.1 ± 1.2**★★ |
| 4 mg/kg | 13.6 ± 1.1 | 5.8 ± 1.5★★ | 4.3 ± 0.8** | 6.7 ± 1.9**★ | 7.8 ± 1.9**★ | 8.4 ± 1.8**★★ |
| 20 mg/kg | 13.9 ± 1.1 | 6.1 ± 1.4★★ | 4.7 ± 1.5★★ | 9.2 ± 1.2**★ | 10.7 ± 1.2**★★ | 10.8 ± 1.1**★★ |

Compared with false modeling group, #P < 0.05, ##P < 0.01;
compared with negative control group, *P < 0.05, *P < 0.01;
compared with the situation before intervention, ★P < 0.05, ★★P < 0.01. (similarly hereafter)

③ Observation on the Influence of Koumine on Hyperalgesia of Adjuvant Arthritis Mice 30 min after intragastric administration, the phlogogenic paw thermal withdrawal latency of the mice in each group was determined by photo-thermal dolorimeter to reflect animals' hyperalgesia status.

Figures 1, 3:
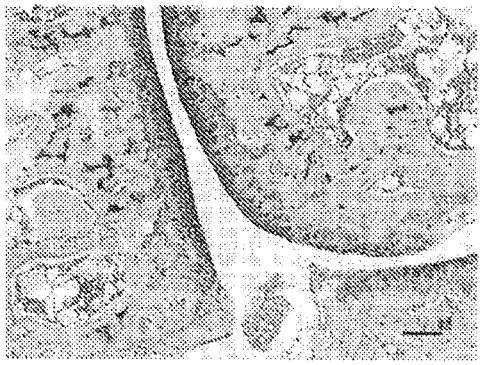
Figures 2, 3:
Figure 3:

(2) Observation on the Influence of Koumine on Joint Pathology Damage of Adjuvant Arthritis Mouse The mice were killed when intervention finished (Day 19), and ankle joints were taken to conduct HE staining pathological examination 3.2 The Influence of Koumine on Joint Pathology Damage of Adjuvant Arthritis Mice The mice joint pathology damage of each group is as shown in FIG. 3. The results show that koumine can improve the inflammatory cell infiltration, synovial hyperplasia, bone destruction or the like of adjuvant arthritis mice joints in a dose dependent manner, indicating koumine has an effect of reversing the pathological changes of adjuvant arthritis.

Overall, koumine improves the symptoms of adjuvant arthritis (body weight reducing, swelling, hyperalgesia etc.) and reverses joint pathological changes in a dose dependent manner, which indicating koumine has the effect of treating autoimmune diseases involving bones and joints including rheumatoid arthritis, spondylitis ankylopoietica etc.

Example 2

The Therapeutic Effect of Koumine on Rat Type II Collagen-Induced Arthritis

Type II collagen-induced arthritis rat model is an animal model used by U.S. Food and Drug Administration for screening drugs treating rheumatoid arthritis, is an acknowledged classical model for researching human rheumatoid arthritis. On type II collagen-induced arthritis rat model, Example 2 uses type II collagen antibody (a golden index assessing the efficiency of drug treatment on rheumatoid arthritis), arthritis symptoms (the condition, body weight, degree of paw swelling, arthritis index and hyperalgesia of rats), joint pathological changes (X-ray radiography and HE staining observation) as indicators to illustrate the therapeutic effect of koumine on autoimmune diseases involving bones and joints including rheumatoid arthritis, spondylitis ankylopoietica etc.

1. Materials
1.1 Animals

Male Wistar rat of clean grade, 130~150 g, purchased from Shanghai Slac Laboratory Animal Co., Ltd., License No.: SCXK (Shanghai) 2010-0005.

1.2 Drugs and Reagents

Koumine (the same as in Example 1). Complete Freund's adjuvant, incomplete Freund's adjuvant, and chicken type II collagen, purchased from Sigma Company. Glacial acetic acid, purchased from Beijing Chemical Reagent Company. Amethopterin, purchased from Shanghai Pharmaceuticals Co., Ltd. Sevoflurane, purchased from Jiangsu Heng Rui Medicine Co., Ltd. Pentobarbital sodium, purchased from Shanghai No. 2 Chemical Reagent Factory. Rat serum anti-type II collagen enzyme linked immunosorbent assay kit, purchased from U.S. Chondrex Company.

1.3 Laboratory Instrument

Von-frey electromechanical pain threshold detector, purchased from IITC Life Science. RT-6000 microplate reader, purchased from U.S. Biotek. Digital X-ray camera, purchased from PHLIPS ELEVA VS.

2. Procedures

Under aseptic conditions, 10 mg chicken type II collagen protein was fully mixed with 5 ml 10 mM glacial acetic acid solution, and stirred overnight in refrigerator at 4° C. to fully dissolve it. It was mixed with complete Freund's adjuvant in equal volume in ice bath to fully emulsify into an emulsion with a collagen concentration of 1 mg/ml.

Wistar rats are divided into a modeling group and a false modeling group. After the modeling group rats were narcotized with intraperitoneal injection of pentobarbital, the above emulsion was injected intracutaneously at 3 to 4 positions at back, tail root or the like, 0.3 ml for each, an primary immunity was carried out. After 7 days, a secondary immunity was carried out, the emulsifying agent complete Freund's adjuvant of initial immunity was replaced with incomplete Freund's adjuvant, 0.1 ml the emulsion was injected under sevoflurane inhalation anesthesia wherein the injection position is different from the last time. In false modeling group, the emulsion was replaced with solvent glacial acetic acid solution.

Successfully modeled rat in the modeling group were randomly divide into 5 groups: low, middle, high-dose koumine treatment group, positive control group, negative control group, 10 rats for each group. Beginning from Day 21 after modeling, corresponding intervention was carried out as following in 10 days continuously: 0.6, 3, 15 mg/kg koumine were intragastrically administered to the low, middle, high-dose koumine treatment group respectively, 1 time every day; 1 mg/kg amethopterin was administered to the positive control group, 1 time every 3 days, equal volume of physiological saline was administrated for the remained days; equal volume of physiological saline was administrated to the negative control group.

Observation Indicators:

(1) Observation on the Influence of Koumine on Rat Type II Collagen Antibody of Type II Collagen-Induced Arthritis Rats of each group were killed after intervention finished, phlebotomize from vena cava, and serum enzyme linked immunosorbent assay was employed to observe rat serum type II collagen antibody level.

(2) Observation on the Influence of Koumine on the Symptoms of Type II Collagen-Induced Arthritis Rat ① Observation on the Influence of Koumine on the Condition and Body Weight of Type II Collagen-Induced Arthritis Rat The rats of each group were observed for the change of condition after inflammation, weighted before the inflammation and on Day 7, Day 14, Day 21, and Day 31 after the inflammation, and observed for the changes of body weight of the rats.

Figures 3, 4:

② Observation on the Influence of Koumine on Paw Swelling Degree and Arthritis Indice of Type II Collagen-Induced Arthritis Rat Before intervention and on Day 5, Day 10 during intervention, a paw volumenometer (see FIG. 4) was made according to the literature [Hesong Yang, Shengyu Han, Wei Gao et. al., *Measuring Device for Rat Paw Swelling Volume and Detection Accuracy Control*, Journal of Chengde Medical University, 2002, 19 (2):132-133] to determine the most swelling hind paw of rats of each group as a paw swelling degree index; the condition of arthritis disease of rats of each group was graded with following standard: score of 0: no reddish swelling; score of 1: erythema or mild swelling of little toe joint; score of 2: moderate swelling of toe joint and metatarsophalangeal joint; score of 3: swelling of paw below ankle joint; score of 4: swelling of whole paw including ankle joint. The arthritis index is the cumulative scores of joints of four limbs.

③ Observation on the Influence of Koumine on the Hyperalgesia of Type II Collagen-Induced Arthritis Rat 1 hour after intragastric administration, the thermal withdrawal latency of each group was determined by the photothermal dolorimeter; the mechanical pain threshold of rats of each group was determined by Von-frey electromechanical pain threshold detector, thus the condition of thermal hyperalgesia and mechanical hyperalgesia of rats of each group was observed.

(3) Observation on Influence of Koumine on Joint Pathological Change of Type II Collagen-Induced Arthritis Rat ① X-Ray Radiographic Observation on Influence of Koumine on Joint Pathological Change of Type II Collagen-Induced Arthritis Rat 9 days after intervention, the rats of each group was narcotized, X-ray camera was used to take lateral position and anteroposterior X-ray pictures of rat's hind limbs, and the condition of the joint pathological change of rats of each group was observed.

② Observation on the Influence of Koumine on Joint Pathological Change of Type II Collagen-Induced Arthritis Rat Using HE Staining Histochemistry The rats of each group were killed 10 days after intervention, the ankle joints of left hind limbs were picked off to conduct HE staining, and the pathological change was observed and scored. Scoring standards is as following: score of 0: joints have normal structures, such as a joint space, a cartilage, a bone and a synovial tissue etc.; score of 1: ciliums formation, a mild inflammation of joint occurs in joint tissues, synovial hyperplasia exists, the number of blood vessels increases, small inflammatory cell focus exists and no cartilage and bone is eroded and damaged; score of 2: some cartilages of joints are eroded and damaged, moderate inflammation of joint exists, there are a large amount of inflammatory cellular infiltration, serious synovial hyperplasia and pannus form, no bone and joint structure damage; score of 3: severe pannus forms, there are a wide range of cartilage eroded and damaged, visible bone damages, and joint structure damages.

Figures 3, 4, 5:
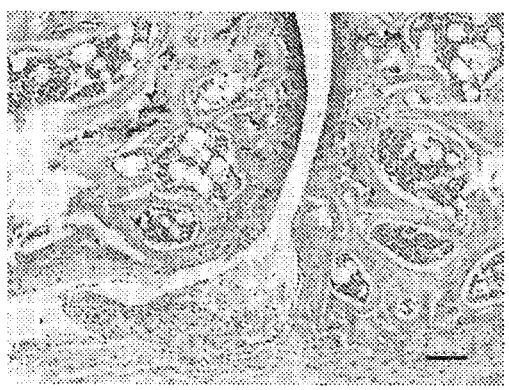

3. Results 3.1 The Influence of Koumine on Rat Type II Collagen Antibody of Type II Collagen-Induced Arthritis Rat The serum type II collagen antibody levels of rats of each group when the intervention finished are shown as in FIG. 5, the results show that koumine has a significantly antagonistic effect on type II collagen antibody level increase of type II collagen-induced arthritis rat in a dose dependent manner, indicating koumine has an effect of inhibiting the generation of rheumatoid arthritis organism autoantibody.

3.2 The Influence of Koumine on the Symptoms of Type II Collagen-Induced Arthritis Rat ① The Influence of Koumine on the Condition and Body Weight of Type II Collagen-Induced Arthritis Rat After modeling, for negative control group, the food intake and activity of rats decreased obviously, fur was lackluster, rats were emaciated, while for koumine treatment group, the condition change of type II collagen-induced arthritis rats can be improved in a dose dependent manner; the body weight of rats of each group on Day 7, Day 14, Day 21, Day 31 after primary immunity are shown in Table 2, the results show that koumine has an antagonistic effect on body weight reducing of type II collagen-induced arthritis rats, even robustness-promoting effect on high-dose group.

TABLE 2

Improving effect of koumine on body weight of type II collagen-induced arthritis rat ($\bar{x} \pm s$, n = 10)

| Group | Body weight before intervention (g) | Body weight after intervention (g) | | | |
|---|---|---|---|---|---|
| | | Day 7 | Day 14 | Day 21 | Day 31 |
| False modeling group | 130.9 ± 7.16 | 164.9 ± 8.72 | 196.5 ± 5.43 | 228.2 ± 8.74 | 241.1 ± 7.06 |
| Negative control group | 125.5 ± 8.30 | 152.7 ± 4.88## | 171.6 ± 5.46## | 193.4 ± 10.20## | 229.2 ± 19.72 |
| Positive control group Koumine treatment | 129.8 ± 6.21 | 154.5 ± 8.36 | 178.2 ± 5.93* | 203.1 ± 9.11* | 227.0 ± 12.68 |
| 0.6 mg/kg | 129.9 ± 8.60 | 154.6 ± 7.20 | 173.1 ± 7.93 | 194.1 ± 16.67 | 235.8 ± 5.00 |
| 3 mg/kg | 126.5 ± 7.92 | 145.1 ± 9.24* | 173.7 ± 4.84 | 202.3 ± 9.57 | 240.2 ± 6.85 |
| 15 mg/kg | 127.8 ± 7.45 | 148.7 ± 8.73 | 176.9 ± 3.86* | 205.1 ± 6.94** | 260.3 ± 11.79** |

Compared with false modeling group,
$P < 0.05$,
$P < 0.01$; compared with negative control group,
*$P < 0.05$,
**$P < 0.01$ (similarly hereafter)

Figures 3, 4, 5, 6:
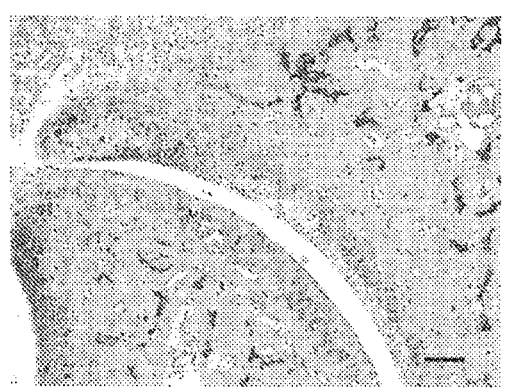
Figure 4:
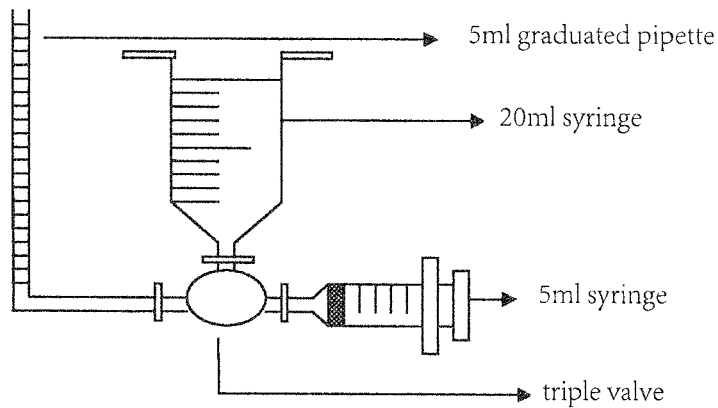
Figure 5:
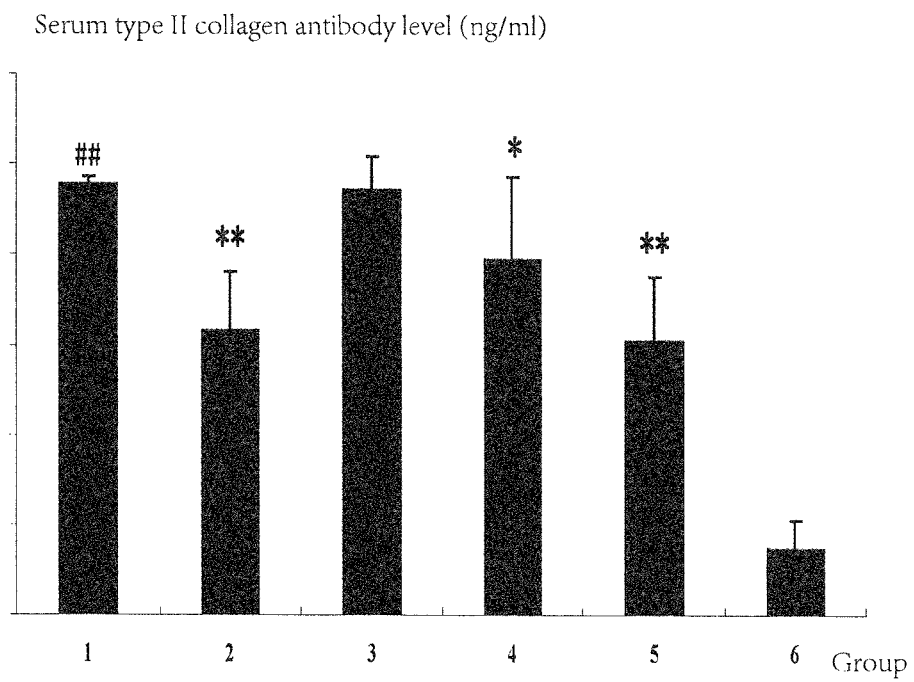
Figure 6:
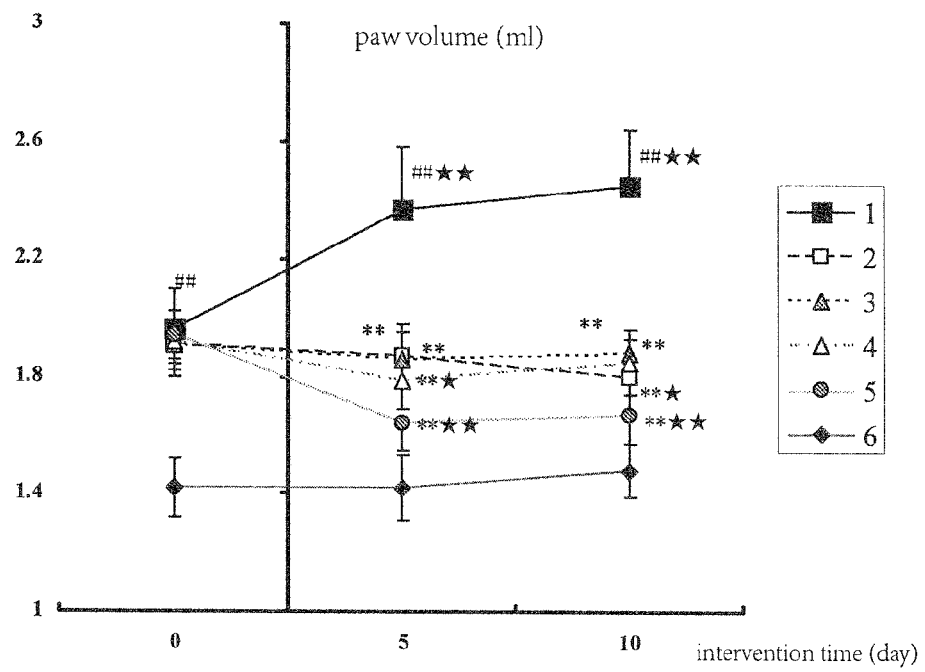
Figure 7:
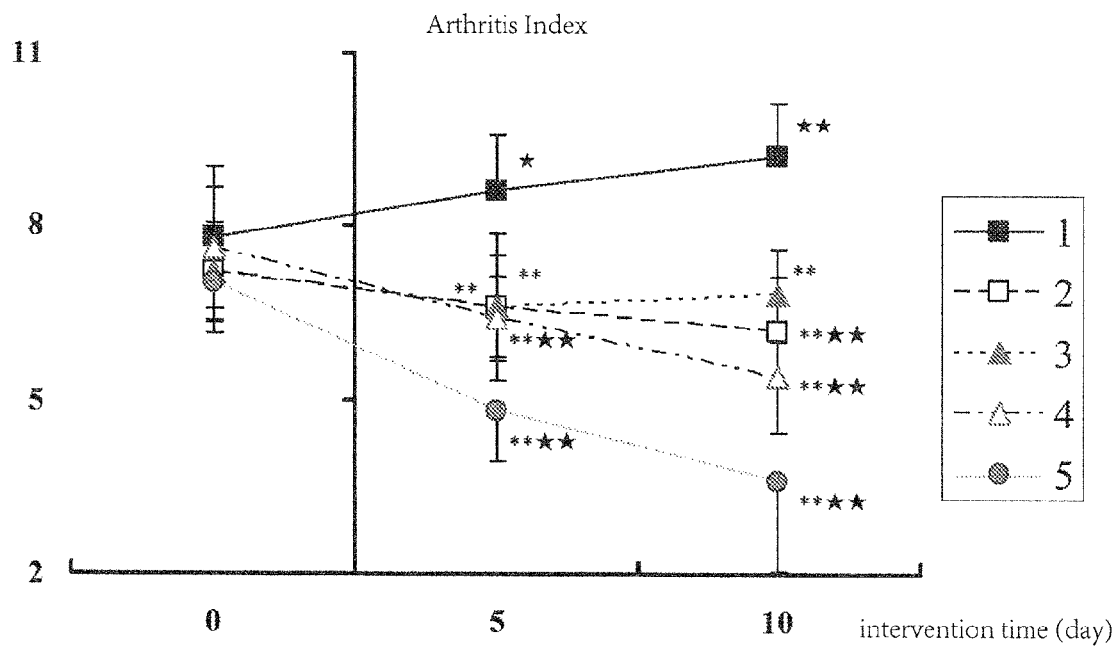
FIG. 7 is a graph of the inhibiting effect of koumine on the arthritis index of type II collagen-induced arthritis rat. In the figure, the horizontal ordinate represents interventional time (day), the vertical ordinate represents arthritis index; 1 is negative control group, 2 is amethopterin positive control group, 3 is 0.6 mg/kg koumine group, 4 is 3 mg/kg koumine group, 5 is 15 mg/kg koumine group; compared with negative control group, $**P<0.01$; compared with the situation before intervention, $\star P<0.05$, $\star\star P<0.01$.

② The Influence of Koumine on Paw Swelling Degree and Arthritis Index of Type II Collagen-Induced Arthritis Rat The paw swelling and arthritis indices of rats of each group before intervention and on Day 5, Day 10 after intervention are shown as in FIG. 6, 7, the results show that koumine relieves the paw swelling and reduces arthritis index of type II collagen-induced arthritis rat in a dose dependent manner.

③ The Influence of Koumine on the Hyperalgesia Status of Type II Collagen-Induced Arthritis Rat The thermal stimulus withdrawal latency and mechanical pain threshold of rats of each group before intervention and on Day 2, Day 4, Day 6, Day 8, Day 10 during intervention were shown as in Table 3-4, the results show that koumine can significantly extend the thermal stimulus withdrawal latency and improve mechanical pain threshold of type II collagen-induced arthritis rats, and the effect of koumine is in a dose-effect relationship, indicating koumine has an effect against the thermal hyperalgesia and mechanical hyperalgesia of type II collagen-induced arthritis.

TABLE 3

Improving effect of koumine on the thermal hyperalgesia of type II collagen-induced arthritis rat ($\bar{x} \pm s$, n = 10)

| | | Thermal stimulus withdrawal latency (second) | | | | |
|---|---|---|---|---|---|---|
| | Before | Intervention | | | | |
| Group | intervention | Day 2 | Day 4 | Day 6 | Day 8 | Day 10 |
| False modeling group | 14.78 ± 1.11 | 14.97 ± 1.33 | 15.43 ± 1.24 | 14.82 ± 1.27 | 15.27 ± 1.18 | 15.92 ± 1.11 |

TABLE 3-continued

Improving effect of koumine on the thermal hyperalgesia
of type II collagen-induced arthritis rat ($\bar{x} \pm s$, n = 10)

| | Before | Intervention | | | | |
|---|---|---|---|---|---|---|
| Group | intervention | Day 2 | Day 4 | Day 6 | Day 8 | Day 10 |
| Negative control group | 7.15 ± 1.70## | 7.33 ± 1.87## | 6.85 ± 1.43## | 6.86 ± 1.57## | 6.22 ± 1.63## | 6.30 ± 1.61## |
| Positive control group | 8.05 ± 1.01 | 8.48 ± 0.73 | 9.15 ± 0.57**★★ | 9.27 ± 1.09**★ | 9.50 ± 1.08**★★ | 10.31 ± 1.21**★ |
| Koumine treatment group | | | | | | |
| 0.6 mg/kg | 7.50 ± 1.34 | 7.81 ± 1.39 | 8.42 ± 1.24* | 10.30 ± 0.73**★ | 8.96 ± 0.81** | 8.62 ± 2.21* |
| 3 mg/kg | 8.03 ± 1.98 | 8.07 ± 1.86 | 9.16 ± 1.18** | 11.18 ± 2.03**★ | 10.40 ± 1.74* | 11.62 ± 1.21**★ |
| 15 mg/kg | 7.68 ± 2.48 | 9.41 ± 0.68** | 10.82 ± 1.07* | 12.98 ± 1.13**★ | 13.44 ± 1.72* | 13.87 ± 1.26**★ |

Compared with the situation before intervening, *P < 0.05, **P < 0.01. (similarly hereinafter)

TABLE 4

Improving effect of koumine on the mechanical hyperalgesia
of type II collagen-induced arthritis rat ($\bar{x} \pm s$, n = 10)

| | Before | Intervention | | | | |
|---|---|---|---|---|---|---|
| Group | intervention | Day 2 | Day 4 | Day 6 | Day 8 | Day 10 |
| False modeling group | 47.50 ± 5.38 | 48.52 ± 4.34 | 49.43 ± 4.92 | 50.03 ± 5.24 | 47.10 ± 5.11 | 51.8 ± 6.14 |
| Negative control group | 21.20 ± 7.05## | 18.53 ± 7.46## | 15.82 ± 6.16## | 13.89 ± 4.50##★ | 12.50 ± 4.21##★ | 13.69 ± 5.55##★ |
| Positive control group | 22.80 ± 5.07 | 19.21 ± 5.12 | 20.00 ± 4.70 | 23.28 ± 6.79** | 23.77 ± 7.37** | 24.37 ± 6.71** |
| Koumine treatment | | | | | | |
| 0.6 mg/kg | 21.40 ± 5.78 | 20.53 ± 5.61 | 23.82 ± 4.64** | 27.94 ± 6.31**★ | 21.00 ± 3.97** | 17.72 ± 3.08## |
| 3 mg/kg | 22.80 ± 5.59 | 28.61 ± 5.32**★ | 30.32 ± 1.82** | 32.04 ± 3.61**★ | 31.53 ± 7.44*** | 29.72 ± 6.80**★ |
| 15 mg/kg | 24.00 ± 5.87 | 36.24 ± 5.39**★ | 37.70 ± 4.37** | 39.55 ± 4.91**★ | 40.32 ± 6.15**★ | 41.95 ± 6.86**★ |

Figures 1, 8:
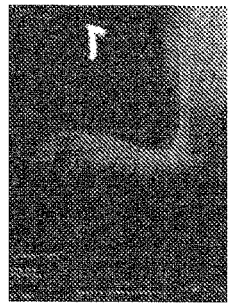
Figures 1, 2, 8:
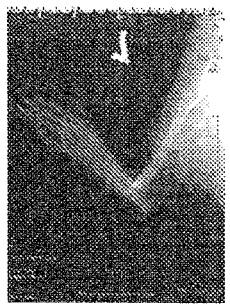
Figures 1, 2, 8:
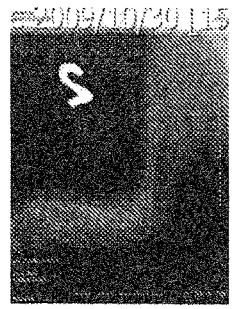
Figures 2, 8:
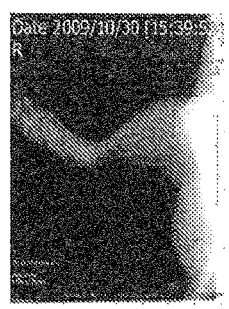
Figures 1, 3, 8:
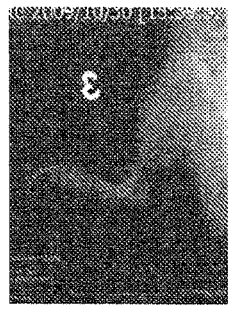
Figures 2, 3, 8:
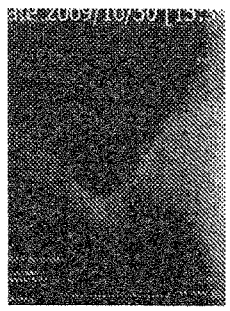
Figures 1, 4, 8:
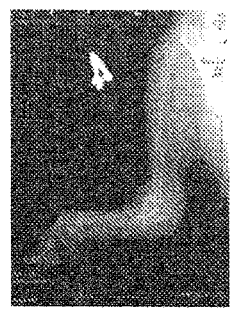
Figures 2, 4, 8:
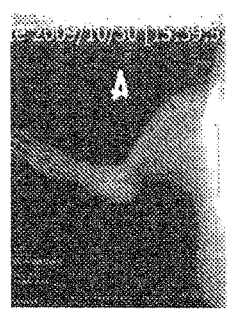
Figures 1, 5, 8:
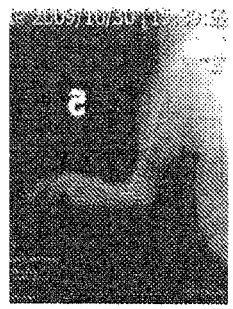
Figures 2, 5, 8:
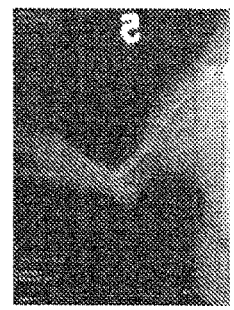
Figures 1, 6, 8:
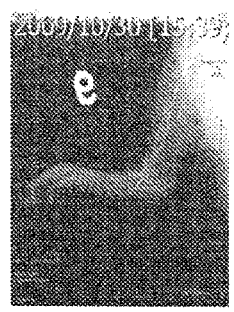
Figures 2, 6, 8:
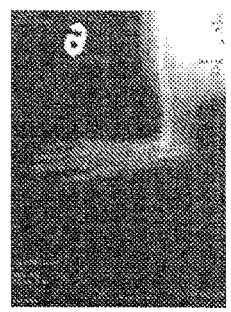

3.3 The Influence of Koumine on the Joint Pathological Change of Type II Collagen-Induced Arthritis Rat ① X-Ray Radiographic Observation on Influence of Koumine on Joint Pathological Change of Type II Collagen-Induced Arthritis Rat Lateral position and anteroposterior X-ray images of joint pathological change of rats of each group are shown as in FIG. 8. The results show that ankle joint soft tissue swelling, blur joint margin of bone, damage of cartilage surface, bone erosion, narrowing and blurring of space between joints of paw toe and between small joints of toes occurs in negative control group; the high dose and middle dose of koumine can both relieve the bone destruction of ankle joint; implying that koumine has an effect of reversing pathological damage of type II collagen-induced arthritis.

Figures 1, 9:
Figures 2, 9:
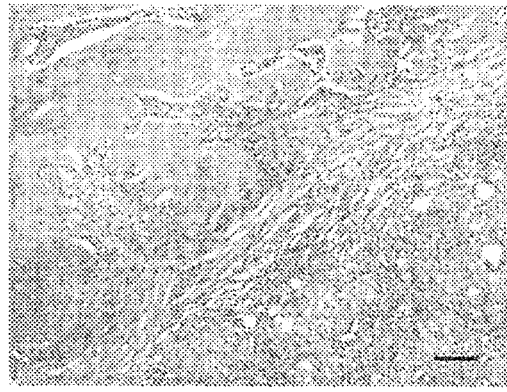
Figures 3, 9:
Figures 4, 9:
Figures 5, 9:
Figures 6, 9:
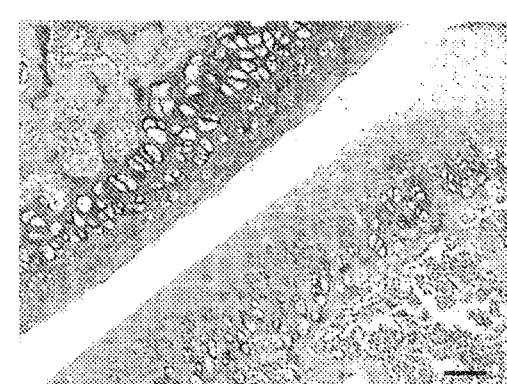
Figure 10:
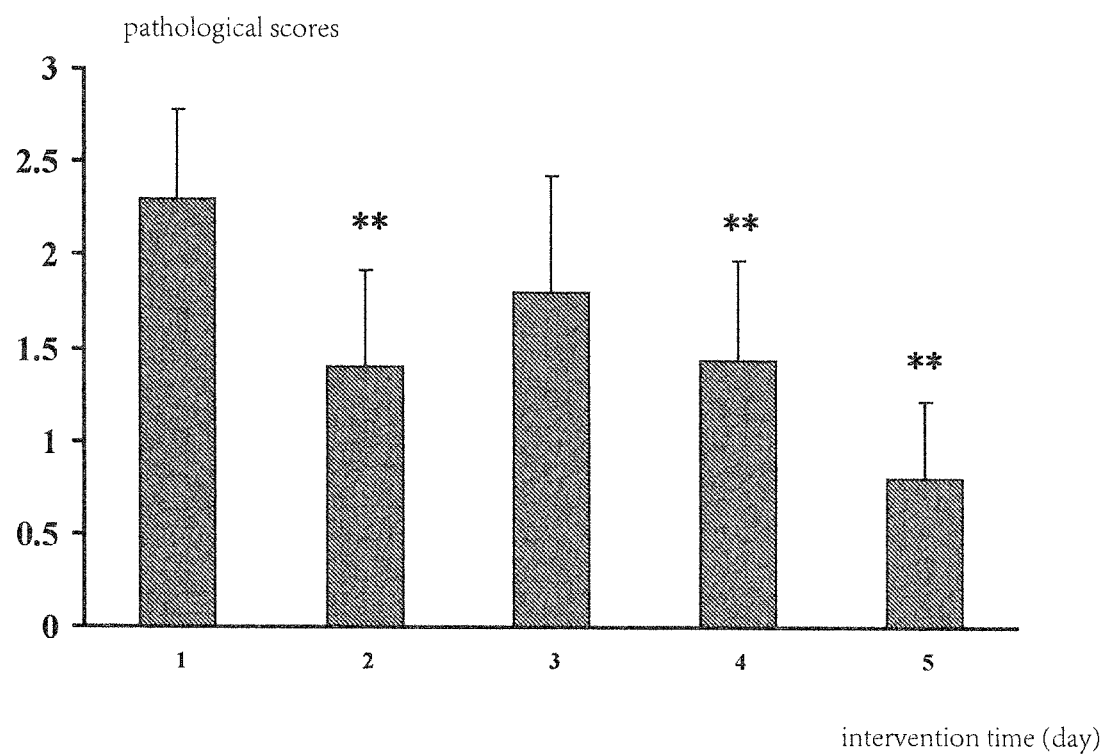
FIG. 10 is a graph of an inhibiting effect of koumine on the pathological scores of type II collagen-induced arthritis rat. In the figure, the horizontal ordinate represents interventional time (day), the vertical ordinate represents pathological scores; 1 is negative control group, 2 is amethopterin positive control group, 3 is 0.6 mg/kg koumine group, 4 is 3 mg/kg koumine group, 5 is 15 mg/kg koumine group; compared with negative control group, **$P<0.01$.

② Observation on the Influence of Koumine on Joint Pathological Change of Type II Collagen-Induced Arthritis Rat Using HE Staining Histochemistry HE staining results and joint scores of the ankle joint pathological change of rats of each group are shown as in FIGS. 9 and 10. The results show that the hyperplastic synovial tissue of rats of negative control group becomes fluffy, blood vessel is hyperplasia, the pannus forms cellulose hyperplasia, inflammatory cell infiltration occurs etc.; koumine can improve the tissue damage of ankle joint, significantly decrease the scores of pathologic change degree of ankle joints of CIA rats. It indicates that koumine has an effect of reversing the pathological damage of type II collagen-induced arthritis.

Overall, koumine can reduce the generation of organism antibody, improve the symptoms (swelling, hyperalgesia, arthritis indices etc.) and reverse joint pathological damage in a dose dependent manner, indicating koumine has the effect of treating autoimmune diseases involving bones and joints including rheumatoid arthritis, spondylitis ankylopoietica etc.

Example 1, 2 are merely the preferred embodiments of the invention, but not in any manner to limit the present invention. Any technical solution without departing from the invention, any simple amendment, equivalent variation and modification base on above embodiments in the light of the technical essence of the invention fall in the scope of the technical solution of the present invention.

The invention claimed is:

1. A method of treating rheumatoid arthritis in a subject, comprising administration of *Gelsemium* alkaloid monomer koumine having the structural formula:

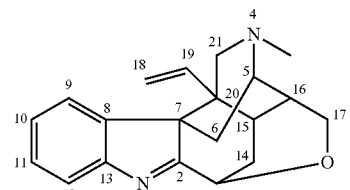

or a pharmaceutically acceptable salt thereof.

* * * * *